(12) United States Patent
Giesen

(10) Patent No.: US 7,803,127 B2
(45) Date of Patent: Sep. 28, 2010

(54) SUPPORTING DEVICE

(76) Inventor: Dirk Giesen, Dürerstrasse 3a, D-76149 Karlsruhe (DE)

(*) Notice: Subject to any disclaimer, the term of this patent is extended or adjusted under 35 U.S.C. 154(b) by 431 days.

(21) Appl. No.: 11/962,385

(22) Filed: Dec. 21, 2007

(65) Prior Publication Data
US 2008/0161738 A1   Jul. 3, 2008

(30) Foreign Application Priority Data
Jan. 3, 2007   (DE) ................. 10 2007 001 053

(51) Int. Cl.
*A61F 5/00* (2006.01)

(52) U.S. Cl. .................. 602/19; 2/44; 128/846; 128/870; 601/5

(58) Field of Classification Search ........ 602/5, 602/16, 19; 2/44, 467; 128/869–870, 873–876; 601/5
See application file for complete search history.

(56) References Cited

FOREIGN PATENT DOCUMENTS

DE   196 52 416         6/1998
FR   2864891 A1 *   7/2005

* cited by examiner

*Primary Examiner*—Patricia M Bianco
*Assistant Examiner*—Keri J Nicholson
(74) *Attorney, Agent, or Firm*—Paul Vincent

(57) ABSTRACT

A supporting device is worn on the human body to counteract the weight force of the torso in a bent-over posture. The weight force of the human torso in a bent-over posture is to be taken up wholly or partly by the supporting device. The user is not to be restricted in his body movements by wearing this supporting device and using its switching functions, as is the case with known models. The use of differently positioned articulation embodiments on the supporting device which is designed ergonomically and adjustable for different body dimensions and is equipped with switching functions is to ensure practical and functional usability for the user. The device is a preventive device for people working in sectors such as building and agriculture who have to perform upward and downward movements of the torso or adopt a bent-over posture very frequently, as strain-relief for the spinal column and to reduce occupational disorders.

13 Claims, 5 Drawing Sheets

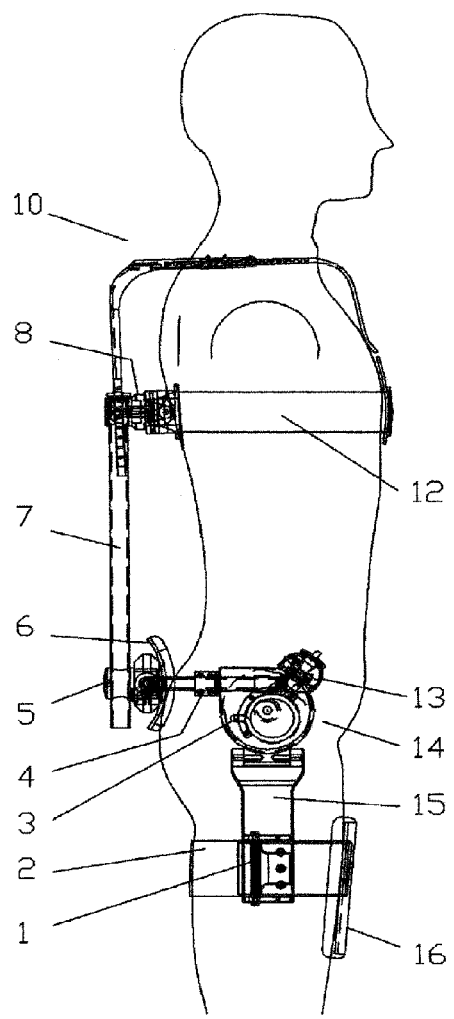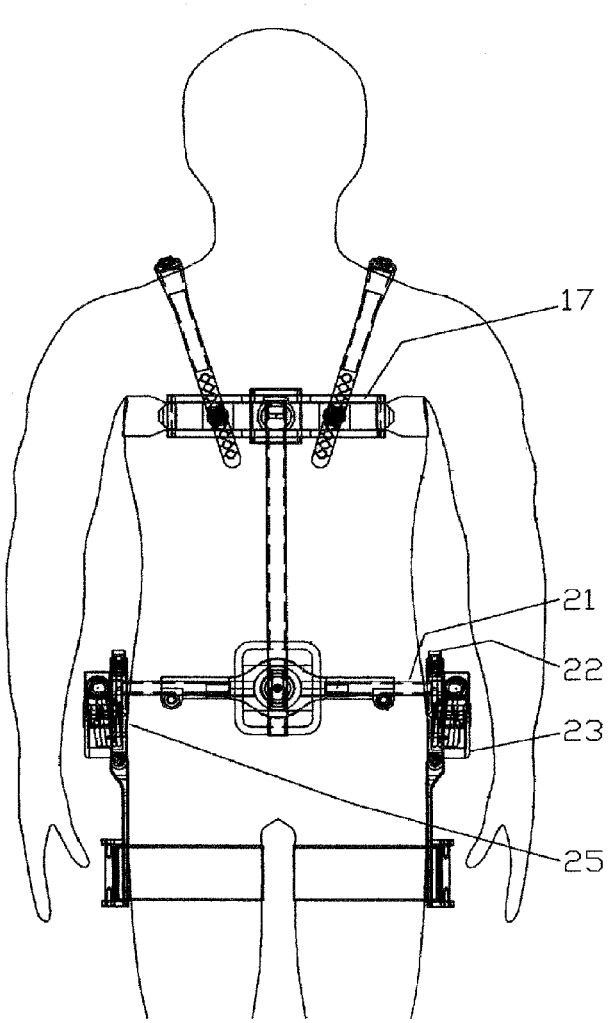

SUPPORTING DEVICE

BACKGROUND OF THE INVENTION

The invention concerns a supporting device that is worn on the human body and counteracts the weight force of the torso in a bent-over posture.

This invention is a preventive device for people working in sectors such as building and agriculture who have to perform upward and downward movements of the torso or assume a bent posture very frequently. It relieves the supportive apparatus and can, in particular, be used for orthopedic application on people already exhibiting symptoms of increased strain on the spinal column due to physically demanding work to protect such people from premature wear, in particular, of the intervertebral disks in the lumbar vertebral region and to maintain performance.

The necessity for the people with the said affliction to be able to use the invention is amply borne out by a statement by the Berufsgenossenschaft (employer's liability insurance association): "One in two pension applications is justified on the grounds of a disorder of the 'spinal column' supportive system."

The closest prior art to the invention are the following applications: DE 10 2004 009 315 A1 describes a device to take the strain off the back when bending or re-adopting an upright posture by means of two curved flat sections that are rigidly horizontally interconnected on the back and worn over the shoulders. From the horizontal connection, a height-adjustable U-shaped curved section extends downward and curves away from the body in the buttock region. A pull strap runs over this curvature and is connected to the horizontal connection and also, below the buttocks in the user's crotch, to a horizontally extending textile strap that has two leg loops, one at each end.

The disadvantage of this design is that this upper part in the shoulder regions cannot be adjusted to individual body dimensions and the lower horizontal connection to the leg loops restricts freedom of movement of the legs. Above all, the strain on the intervertebral disks is increased when the torso is bent due to the design using a pull strap.

DE 196 52 416 A1 describes a device as an orthopedic body brace for supporting the human torso in a bent-over posture with articulations disposed above the hip region that contain, a helical spring and from which supporting arms extend upward on the torso that are connected to the torso by supporting straps as well as supporting arms extending toward the thighs from the articulations on the side of the body that at least partially surround the thighs.

The disadvantage of this design is that the user can only perform walking movements under spring tension, that lateral movements of the torso are not possible while bending the torso without the complete supporting structure losing its position on the body, that the user cannot make lateral leg movements, that, while bending the torso, the lateral torsional forces of the lower supporting arms can be transferred to the upper supporting arms that can rotate laterally away from the body and restrict arm movements.

SUMMARY OF THE INVENTION

The objective was to solve the problem that the following requirements must be met before the supporting device specified in the independent claim could be put to practical use by the people affected who work in sectors in which physically demanding activities are performed in a bent-over posture:

a) The basic structure of the supporting device must both be apt to provide effective relief from strain on the spinal column and solve the following problems.

b) Complete freedom of movement of the user must be ensured while wearing the supporting device.

c) The supporting device must be ergonomically adjustable to different body dimensions and the position of the supporting device on the body must be retained during movements performed while wearing the supporting device.

d) It must be easy for the user to switch off counterforce of the supporting device to enable normal leg movements. The counterforce of the supporting device must take effect at the beginning of the bending action but it must be possible, for example, in the case of users with low body weight, for the counterforce of the supporting device not to take effect before a certain bending radius is reached.

e) It must be possible for the weight force taken up by the supporting device to be functionally transferred to the thighs.

The overall problem is solved by the features of the independent claim. The dependent claims whose characteristics are also intended to be part of the description state beneficial embodiments.

The problem related to aspect a) is solved as follows:

The basic structure of the supporting device essentially comprises two spring boxes constituted as articulations, of which one is located on each side in the hip region. A cantilever extends straight backward in the horizontal direction from the outer half of the articulation of each spring box. These two cantilevers come together in an articulation located in the lumbar vertebral region. From the said articulation, a cantilever extends vertically upward and, at its upper end, adjoins a cross-member in an articulation. This cross-member is ergonomically shaped, lies horizontally against the back, and, at its ends, the chest strap is attached that takes up the weight force of the torso in a bent-over posture. Under the spring boxes, there is one leg upright-member per leg that extends downward on the side of each leg and ends in a horizontal clasp strap.

The problem related to aspect b) is solved as follows:

The dimensions of the components are kept as small as possible. The weight force in a bent-over posture of the torso is essentially transferred through a chest strap in the torso region on to a cantilever extending vertically down the back before being directed outward in the hip region via two horizontally extending cantilevers. Each of these cantilevers ends in an articulation constituted as a spring box that is located against each side of the body, the spring boxes being swivelable about the longitudinal axis of the cantilevers inserted into them.

Under each spring box, a leg upright-member extending downward via an articulation is attached.

The cantilever extending vertically on the back is attached to the articulation located in the lumbar vertebral region such that it can swivel. Moreover, at the upper end, the cantilever ends in an articulation combination that is constituted with a horizontally extending cross-member on the side of the torso and can be rotated in three axes.

The cross-member has two cylindrical guides extending backward, each attached to a shoulder support that can swivel in the longitudinal axis relative to the cross-member.

The problem related to aspect c) is solved as follows:

The two articulations constituted as spring boxes are adjustably fixed by means of one clamp each to the thigh end of the two side cantilevers that are inserted into the spring boxes.

The straight ends of the two cantilevers extending around the buttocks of the user are adjustably routed into the two holders of the articulation in the lumbar vertebral region, where they are locked in position.

The two clasp straps, each of which is connected at one end with a leg upright-member and completely girdles a thigh, can be adjusted in their circumference by means of a clamping device. The cantilever extending vertically on the back can be height-adjusted in its longitudinal axis by means of an adjusting screw that is seated in the articulation located in the lumbar vertebral region. The two shoulder supports, which are each attached to one of the cylindrical guides extending backward from the cross-member such that they can swivel, can be height-adjusted by means of holes in the lower region of the shoulder supports for fixture to the cylindrical guides of the cross-member.

The non-elastic shoulder supports that extend upward from the cross-member and are bent forward in the longitudinal axis over the shoulders ensure that the set position of the supporting device relative to the body is not lost during movements. Due to this rigid implementation and in conjunction with the chest strap positioned against the body, the cross-member, and therefore the entire supporting device, is held in position.

The problem related to aspect d) is solved as follows:

The switching operations are performed at the two articulations constituted as spring boxes. The functions and the structure of the two spring boxes are identical. A spring box consists of a base casing located against the hip at each side and an external cover casing, both having a cylindrical recess and being interconnected via an axle at the centric pivot point. A switching mechanism is attached on the outer radius of the base casing in its longitudinal axis, with which preferably three switching functions are possible. The spring box contains a helical spring that is borne preferably eccentrically with respect to the pivot point of the spring box and is held and guided at its periphery by the shape of the cylindrical recess of the cover casing. A bent leg end of the helical spring is seated in the cover casing of the spring box and is freely movable only in the direction parallel to the longitudinal axis of the pivot point.

The other bent leg end of the helical spring can move freely in the base casing in its direction of torsion in the region in front of the stop bolts, which are separately guided out of the switching mechanism.

The switching mechanism preferably contains two stop bolts in the longitudinal direction with respect to the spring box. These stop bolts are at an angle to each other and are guided such that each can move though a through-hole on the outer radius of the base casing. One compression spring per stop bolt is disposed outside the base casings in the longitudinal axis with respect to the stop bolts and is limited at one end by the base casing and at the other end by the head of the stop bolt.

A rocker is disposed via a pivot point located outside on each base casing centrically between the two stop bolts, which are at an angle to each other. This rocker is constituted in its upward extension as a switch to be operated by hand. For the switching function, the heads of the stop bolts have surfaces at a certain angle at the upper end.

The problem related to aspect e) is solved as follows:

The weight taken up by the supporting device is largely transferred via the torque of the helical springs that are located in the spring boxes onto the leg upright-members that extend downward and fixed to the bottom of the spring boxes via an articulation. The force is thereby transferred to the elastic clasp straps, one end of each clasp strap being fixed to the lower end of each leg upright-member.

Each elastic clasp strap girdles a thigh.

Lateral guides are attached to the leg upright-members in the longitudinal axis of the clasp straps contacting the clasp straps above and below to ensure that the elastic clasp straps remain stable in their longitudinal axis. Moreover, each clasp strap is attached to a thigh plate that additionally stabilizes the clasp straps.

BRIEF DESCRIPTION OF THE DRAWING

FIG. 1 shows a side view of the supporting device in accordance with the invention;

FIG. 2 shows a rear view of the supporting device in accordance with the invention;

DESCRIPTION OF THE PREFERRED EMBODIMENT

An embodiment of the invention is illustrated in the figures.

Figure 5:
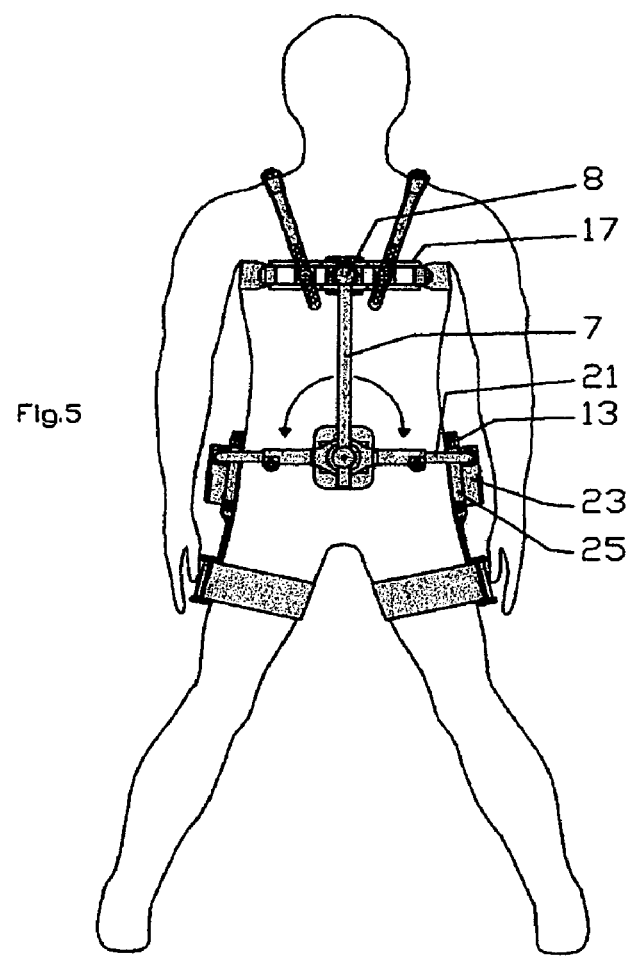
FIG. 5 shows an additional rear view of the supporting device in accordance with the invention.
Figure 4:
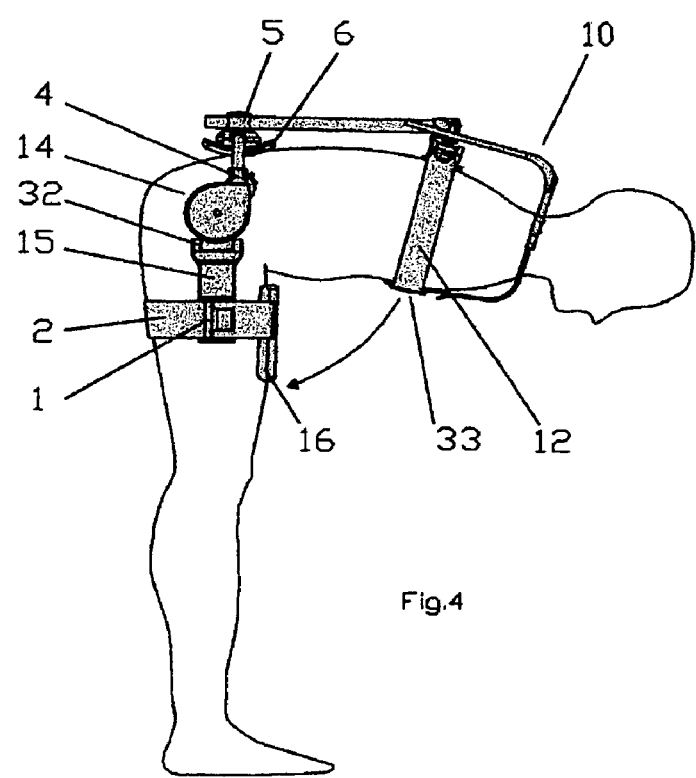
FIG. 4 shows a side view of the supporting device in accordance with the invention in a forwardly bent position.

Assuming the supporting device has been adjusted to the individual body dimensions of the user according to the adjustment options explained in it is then worn on the body as shown in FIGS. 4 and 5.

The user hooks the two shoulder supports (10) onto the body and tightens the chest straps (12) on the breast plate (33). The user then slides, first on one leg, the end of the clasp strap (2) lying against the thigh from behind between the leg upright-member (15) and the shaft (1) of the clasp, then he adjusts the thigh plate (16) on the front on the leg, then he swings the tongue of the clasp shaft (1) forward. Due to the eccentric bearing of the clasp shaft (1), the separation between the leg upright-member (15) and the clasp shaft (1) is reduced. This locks the clasp strap (2). The user then performs this operation on the other leg. The supporting device is now applied to the body and the user can now choose between three gears that are designated "gear 1", "neutral" and "gear 2".

Figure 3:
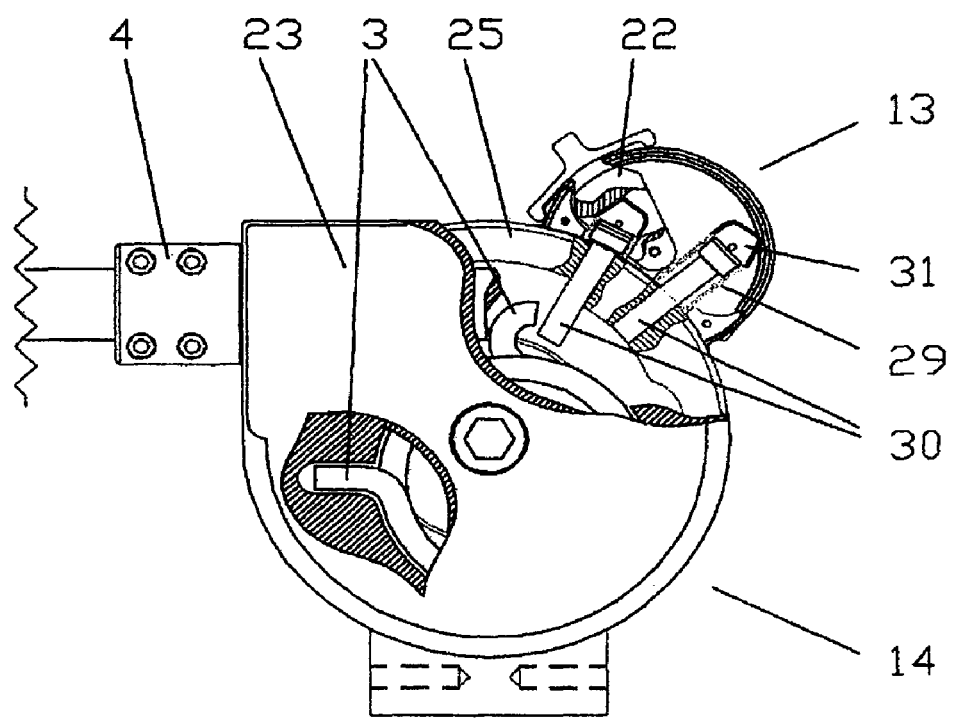
FIG. 3 shows a detail of the spring box in the supporting device in accordance with the invention.

FIG. 3 illustrates the following embodiment.

Setting the gears should be performed simultaneously on both spring boxes (14). The functional sequence is described here for one switching mechanism (13) and spring box (14).

In neutral, the rocker (22) is in the center, exactly in the bisector between the two stop bolts (30). The stop bolts (30) are pressed upward by the compression springs (29) and their heads (31) touch the housing of the switching mechanism (13). In neutral, the upper bent leg of the helical spring (3) is freely movable in the direction of torsion. If the user bends the torso forward or performs walking movements, the helical spring (3) is entrained eccentrically with respect to the pivot point of the spring box (14) guided by the outer casing (23) of the spring box (14), but there is no torque that acts as a counterforce. Basically, switching between gears is only performed if the user's torso is in an upright posture. The user switches to "gear 1" by moving the switch of the rocker (22) backward as seen from the body of the user. This slides the lower surface of the rocker (22) over the head (31) of the stop bolt (30) and presses this against the compression spring (29) into the space of the cylindrical recess of the base casing (25) and, at a certain radius, moves the end of the switch over a projection of the base casing (25), where it is retained by the abrupt surface of the head (31). Thus the upper bent leg of the helical spring (3) is now in front of the stop bolt (30) in its direction of torsion. If the user now bends the torso forward, the chest strap (12) takes up the weight force which, in turn, is transferred to the cantilevers (7,21). This sets the outer cover casing (23) of the spring box (14) into rotary motion.

This rotary motion causes the upper end of the leg of the helical spring (3) to contact the end of the stop bolt (30) protruding into the base casing (25). The torque of the helical spring (3) now counteracts the weight force of the torso and is transferred to the leg via the leg upright-member (15) and the clasp strap (2) with the thigh plate (16).

If the user wants to switch from "gear 1" to "neutral", he slides the switch of the rocker (22) forward, pressing the lower surface of the rocker (22) against the head (31) of the stop bolt (30) and pressing the said head slightly downward minimally counteracting the resilient force of the compression spring (29). This pushes the head in a radius to the centrically located pivot point of the rocker (22) over the head surface of the stop bolt (30) into the position exactly in the bisector between the stop bolts (30). The released stop bolt (30) is pressed upward by the resilient force out of the cylindrical recess of the base casing (25) into the switching housing, leaving the path for the upper leg of the helical spring (3) unobstructed so that no torque can arise.

Setting "gear 2" is analogous to setting "gear 1", except that the switch of the rocker (22) is pushed completely forward.

FIGS. 4 and 5 show that when the torso is bent over, the padding (6) that is located on the articulation (5) in the lumbar vertebral region is entrained in a curve with respect to the spinal column and slides minimally over the user's clothing due to its curvature and the smooth surface.

The shoulders, which fall forward somewhat in a bent-over posture, are compensated for by the shoulder supports (10) because there is one compression spring each between these and the cross-member (17) which hold the shoulder supports (10) in an aligned position in the longitudinal axis with respect to the cross-member (17). The user of the supporting device can move his legs back and forth due to the articulations constituted as spring boxes (14), of which there is one on the side of each hip, and he can move his legs to the side due to lateral cantilevers (21) inserted into the spring boxes (14) that are firmly held by a clamp (4) and that fix the spring box in the transverse direction such that it can swivel and also due to the leg upright-members (15) that each are connected to a spring box (14) via an articulation (32).

Moreover, the user can swivel the torso to the side due to the articulation (5) that is located at the back in the lumbar vertebral region. The upper articulation combination (8) allows the user to rotate the torso in three axes without restrictions while wearing the supporting device, in accordance with the movements of the spinal column.

Figure 6:
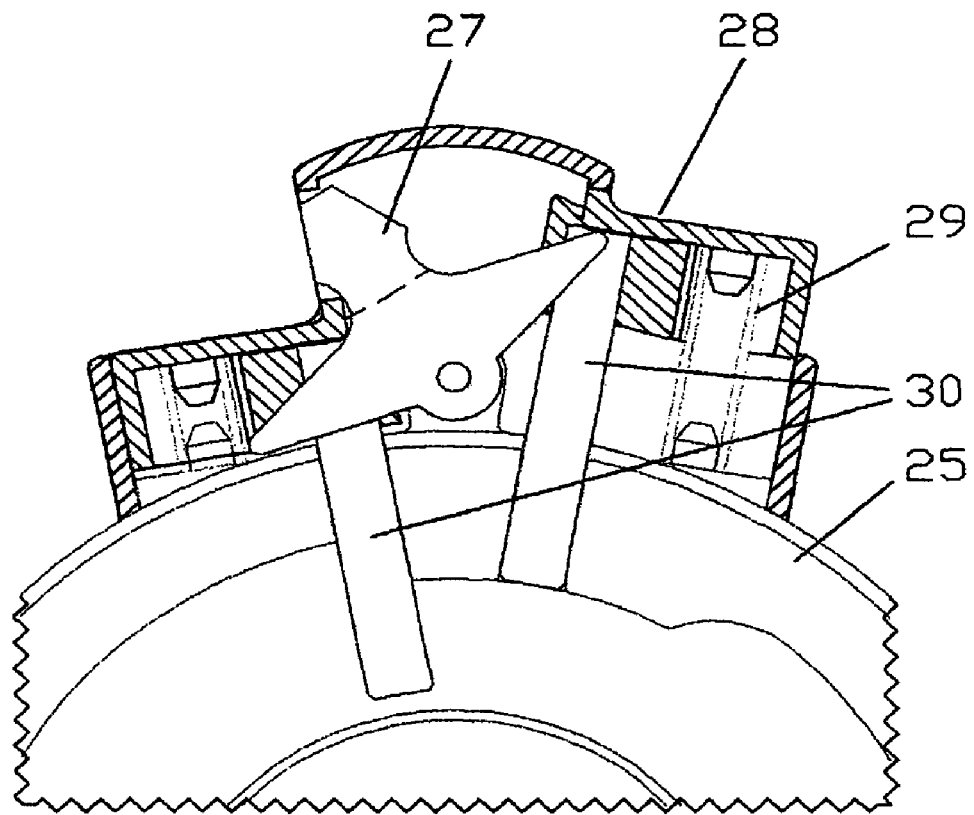
FIG. 6 shows an additional embodiment of the spring box in the supporting device in accordance with the invention.
Figure 7:
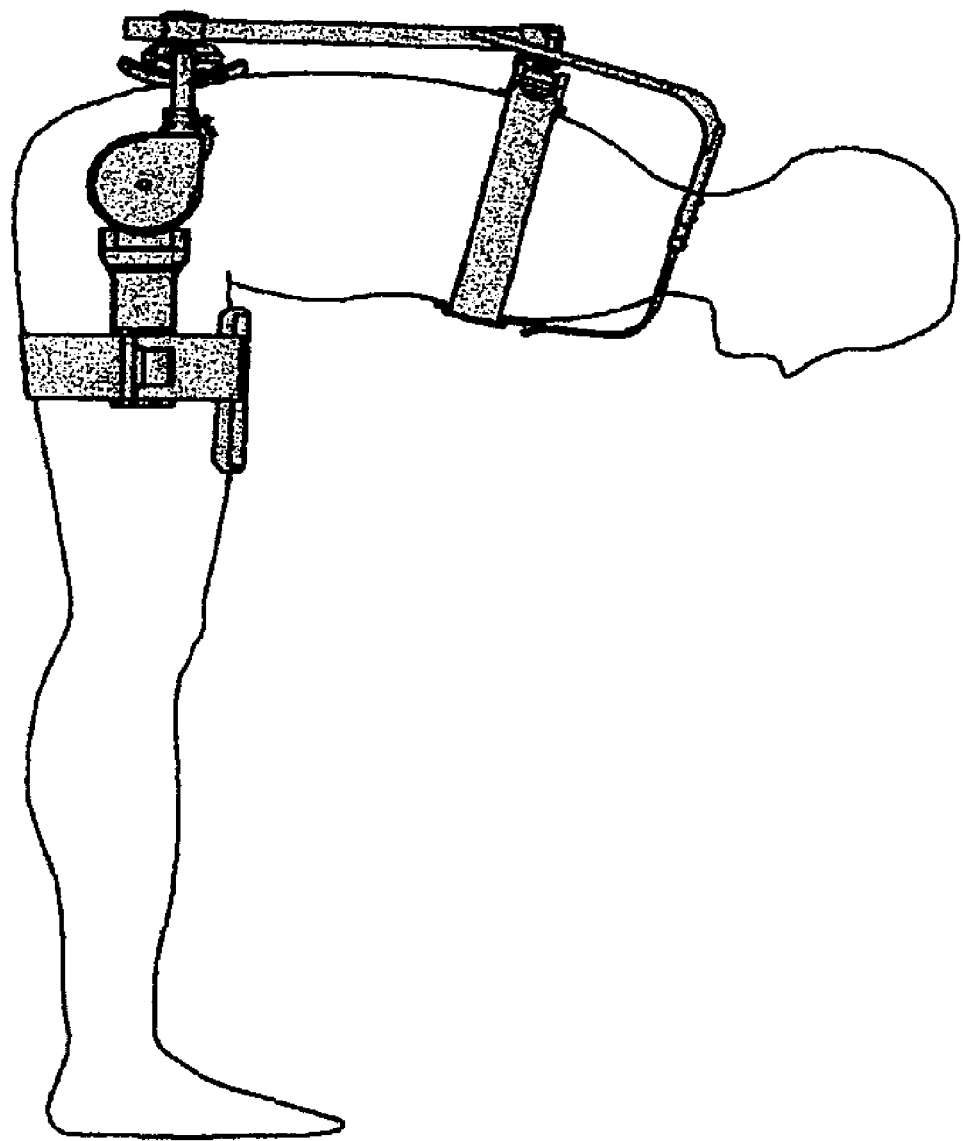
FIG. 7 shows an additional side view of the supporting device in accordance with the invention in a bent position.

As an embodiment, FIG. 6 shows another way of moving the stop bolts (30) to the gears "gear 1", "neutral", "gear 2". The switching mechanism consists of two pushbuttons (28) that each contain a stop bolt (30) and a compression spring (29). When one pushbutton (28) is pressed, a stop bolt (30) is pushed against the resilient force of a compression spring (29) into the cylindrical recess of the base casing (25). The contour of the pushbutton (28) entrains a pivoted rocker (27) in the center on the outer radius of the base casing (25), each with two lateral arms engaging in a pushbutton (28). Shortly before the lower end position of the pushbutton (28), the upper part of the rocker (27) swivels into an upper projection of the pushbutton (28) and fixes it in the end position. The user switches to neutral by slightly pressing the non-depressed higher pushbutton (28). This presses the contour of the upper pushbutton (28) onto the higher arm of the rocker (27) whose upper part, in turn, swings out of the contour projection of the latched pushbutton (28) toward the pressed pushbutton (28), thus clearing the path for the fixed pushbutton (28), which is pushed into the upper position by the compression spring. Setting "gear 2" is performed analogously to setting "gear 1", but with the other pushbutton.

The advantages achieved with the invention are, in particular, that the support device by its structure, as stated in claim 1, provides effective strain-relief for the spinal column and the structure of the support device does not hinder the movements of the user. Due to the articulations of the support device stated in claims 1 to 3 and 6 to 9, the user is able to move without restriction, which is indispensable for practical use in many sectors. According to claims 3 to 5, the switching functions can be performed easily. The user can switch to neutral in order to move without restriction without having to remove the supporting device.

A further advantage is the existence of "gear 2" stated in claims 3 and 5. The user can set this gear to have the counterforce of the supporting device applied a little later, and perform small walking movements with this gear applied.

I claim:

1. A supporting device for wear on a human body to counteract a weight force of a torso in a bent-over posture, the supporting device comprising:
   a first spring box adapted to be disposed at a first hip region;
   a second spring box adapted to be disposed at a second hip region;
   a first horizontally extending lateral cantilever inserted within said first spring box;
   a second horizontally extending lateral cantilever inserted within said second spring box;
   a first clamp cooperating with said first spring box and said first cantilever, wherein said first cantilever can pivot and be adjusted with respect to a straight path thereof;
   a second clamp cooperating with said second spring box and said second cantilever, wherein said second cantilever can pivot and be adjusted with respect to a straight path thereof, wherein said first and said second cantilevers extend from said first and said second spring boxes straight back and then around buttocks of a user and are length-adjustable along respective longitudinal axes thereof;
   a lumbar articulation located at a height of a lumbar vertebrae, said lumbar articulation having a first laterally horizontally departing holder for accepting and locking an inserted straight end of said first cantilever and a second laterally horizontally departing holder for accepting and locking an inserted straight end of said second cantilever, each of said first and said second holders having a guide slot and an adjusting screw;

a pivoting cantilever extending from said lumbar articulation and locked in position by means of a lumbar screw, said pivoting cantilever adapted to extend upward on a back, and being height-adjustable along a longitudinal axis thereof; and an upper articulation cooperating at chest height with said pivoting cantilever to slide and rotate for height adjustment with respect to a longitudinal axis of said first and said second cantilevers, wherein the weight force of the torso is taken up by an upper part of the supporting device and is transferred to a lower part thereof via said first and said second spring boxes to rest upon thighs, thereby relieving strain on intervertebral disks of lumbar vertebrae.

2. The supporting device of claim 1, wherein a downward extending leg upright-member is attached to a lower side of each of said first and said second spring boxes via an articulation, wherein, at a lower end of each leg upright-member, an elastic clasp strap is connected at one end and can completely girdle the thigh, wherein a clasp shaft that is transverse with respect to a longitudinal axis of said clasp straps is eccentrically movably connected to each leg upright-member to function as a strap clasp, each of said clasp shafts having one small tongue for manual operation, with each clasp strap containing a thigh plate structured to slide along a longitudinal axis thereof.

3. The supporting device of claim 1, wherein said first and said second spring boxes comprises four subunits, having articulations comprising a base casing adapted to be applied to the hip and an outer cover casing, each with a cylindrical recess and interconnected via a centric pivot point thereof, with one switching mechanism each being located at a top on said base casings and having three switching functions, wherein one helical spring is borne eccentrically or centrically with respect to each centric pivot point of said first and said second spring boxes, said spring being held and guided at a periphery by a shape of said cylindrical recess of said cover casing.

4. The supporting device of claim 3, wherein a bent leg end of each of said helical springs is seated in said cover casing of said first and second spring boxes and is only freely movable in a direction parallel to a longitudinal axis of said centric pivot point, wherein an other bent leg end of each of said two helical springs is located in said base casing of a respective said first and said second spring boxes in a torsion direction of said helical springs at a region in front of stop bolts, said stop bolts being separately guided out of said switching mechanisms.

5. The supporting device of claim 3, wherein each said switching mechanism has two stop bolts extending in a longitudinal direction with respect to each respective one of said first and second spring boxes, said stop bolts extending at an angle with respect to each other and guided such that each can move though a through-hole on an outer radius of said base casings, wherein, outside said base casings in a longitudinal axis with respect to said stop bolts, is one compression spring per stop bolt that is limited at one end by said base casing and at an other end by a head of said stop bolt, a rocker being disposed via a pivot point located outside on each base casing centrically between said two stop bolts, said rocker being constituted in an upward extension as a switch to be operated by hand, wherein heads of said stop bolts have angled surfaces at upper ends thereof.

6. The supporting device of claim 1, wherein said upper articulation is constituted as an articulation combination for rotation about three axes, an articulation end thereof extending toward the torso being designed with an ergonomically shaped cross-member adapted to be located on the back that contains a chest strap and two shoulder supports.

7. The support device of claim 6, wherein said two shoulder supports each consist of two parts on which two backward extending cylindrical guides are disposed from said cross-member, each being, at longitudinal axis back sections thereof that are each movable against a compression spring, height-adjustable, angled in said longitudinal axis, and pivotable, wherein said two back sections consist of a robust, non-elastic structure and horizontal surfaces of each said back section contain an elastic shoulder section that is slidable in the longitudinal axis, can be locked in position, and is angled.

8. The supporting device of claim 1, wherein a padding is attached to said lumbar articulation at a side of the lumbar vertebrae and having a curvature above and below, away from a body, at least in a vertical direction.

9. The supporting device of claim 1, wherein said first and said second clamps firmly hold said first and said second lateral cantilevers each engaging in an inner annular slot in annular projections of said spring boxes with a certain degree of play.

10. The supporting device of claim 1, wherein said upper articulation comprises a ball-and-socket articulation.

11. The supporting device of claim 3, wherein gears can also be set manually by inserting stop bolts into through-holes of said base casings.

12. The supporting device of claim 3, wherein each of said switching mechanisms is constituted such that individual gears are inserted using manually operated pushbuttons, wherein said pushbuttons each contain one stop bolt and one spring, wherein a rocker is disposed centrically with respect to said stop bolts on an outer radius of said base casing, such that it can pivot, with lateral arms guided onto said pushbuttons.

13. The supporting of claim 3, wherein said helical springs have a rectangular special section for a changing torque.

* * * * *